United States Patent [19]

Nicholas et al.

[11] Patent Number: 4,501,148

[45] Date of Patent: Feb. 26, 1985

[54] MANUAL MUSCLE TESTER

[76] Inventors: James A. Nicholas, 22 Cayuga Rd., Scarsdale, N.Y. 10583; Richard Krukowski, 205 Washington Ave., Chatham, N.J. 07928

[21] Appl. No.: 337,304

[22] Filed: Jan. 5, 1982

[51] Int. Cl.³ ............................ G01L 5/02; G01L 1/18
[52] U.S. Cl. ................................... 73/379; 73/862.53; 73/862.67
[58] Field of Search ................ 73/379, 862.53, 862.58, 73/862.64, 862.65, 862.67, 862.62; 128/774

[56] References Cited

U.S. PATENT DOCUMENTS

| | | |
|---|---|---|
| 2,472,047 | 5/1949 | Ruge .............................. 73/862.65 X |
| 2,680,967 | 6/1954 | Newman ....................... 73/862.58 X |
| 2,844,959 | 7/1958 | Grass ............................ 73/862.65 X |
| 3,323,366 | 6/1967 | DeLorme, Jr. et al. . |
| 3,375,717 | 4/1968 | Impellizzeri et al. . |
| 3,387,493 | 6/1968 | Strittmatter . |
| 3,464,259 | 9/1969 | Farr . |
| 3,465,592 | 9/1969 | Perrine . |
| 3,474,776 | 10/1969 | O'Brien . |
| 3,572,700 | 3/1971 | Mastropaolo . |
| 3,577,779 | 5/1971 | Laimins . |
| 3,670,573 | 6/1972 | Kroemer . |
| 3,680,386 | 8/1972 | Cannon . |
| 3,744,480 | 7/1973 | Gause et al. . |
| 3,745,990 | 7/1973 | Neis . |
| 4,212,197 | 7/1980 | Kawai et al. . |
| 4,244,213 | 1/1981 | Marcinkiewicz ................ 73/862.23 |
| 4,307,608 | 12/1981 | Useldinger et al. .................. 73/379 |

FOREIGN PATENT DOCUMENTS

| | | |
|---|---|---|
| 2544160 | 4/1977 | Fed. Rep. of Germany ... 73/862.65 |
| 0909840 | 11/1962 | United Kingdom . |
| 227642 | 9/1968 | U.S.S.R. ........................... 73/862.65 |

OTHER PUBLICATIONS

Petrofsky-"Digital Controlled Handgrip Dynamometer for Isometric Performance Studies", NAECON. 1981, May 1981, pp. 574-580.

The Strain Gage Primer, McGraw-Hill Book Co., 2nd Ed., 1962, pp. 229-237.

Wakim et al., Objective Recording of Muscle Strength, Archives of Physical Medicine, Feb. 1950, pp. 90-99.

Lowman, Muscle Strength Testing, 20 The Physiotherapy Review, 69-71, (1940).

Bennett, Muscle Testing, 27 The Physiotherapy Review, 242-243, (1946).

Kroemer et al., Towards Standardization of Muscle Strength Testing, 2 Medicine and Science in Sports, 242-230, (1970).

Gonnella, The Manual Muscle Test in the Patient's Evaluation and Program for Treatment, 34 The Physical Therapy Review, 16-18.

Lilienfeld, A Study of The Reproductibility of Muscle Testing and Certain Other Aspects of Muscle Scoring, 34 The Physical Therapy Review, 279-289, (1954).

Spackman, Muscle Strength Testing Unit, (Approx. 1971), journal unknown.

Hunsicker et al., Instruments to Measure Strength, 26 The Research Quarterly, 408 (about 1955).

(List continued on next page)

Primary Examiner—Charles A. Ruehl
Attorney, Agent, or Firm—Brumbaugh, Graves, Donohue & Raymond

[57] ABSTRACT

A portable manual muscle tester has an external actuator, a case capable of being held in one hand and a digital display indicating peak force applied to the actuator. Strain gages connected in a bridge circuit are located on a flexure contacted by the actuator. The flexure is a cantilever beam shaped to fit the small case and to prevent reflected or mounting stresses being registered in the force display. The circuit from the strain gage bridge to the display includes an instrumentation amplifier followed by a peak freeze circuit that includes operational amplifiers and a peak freeze capacitor. The peak freeze capacitor provides a voltage that is read by a digital volt meter. A further operational amplifier connected as an integrator feeds back from the peak freeze circuit to an input of the instrumentation amplifier to reset the meter to zero after the displayed force reading has been noted.

21 Claims, 6 Drawing Figures

OTHER PUBLICATIONS

Nicholas et al., Factors Influencing Manual Muscle Tests In Physical Therapy, 60-A Journal of Bone and Joint Surgery, 186-190, (1978), See into p. 3-4 for shortcomings.

Nicholas et al., Neurophysiologic Inhibition of Strength Following Tactile Stimulation of the Skin, 8 American Journal of Sports Medicine, 181-186, 1980.

Saraniti et al., The Relationship Between Subjective and Objective Measurement of Strength, 2 Journal of Orthopedic and Sports Physical Therapy, 15-19, 1980.

Clarke, Objective Strength Tests of Affected Muscle Groups Involved in Orthopedic Disabilities, 19 Research Quarterly, 118, (1948).

Clarke, Improvement of Objective Strength Tests of Muscle Groups by Cable-Tension Methods, 22 Research Quarterly, 399, (1951).

Komi et al., Effect of Eccentric and Concentric Muscle Conditioning on Tension and Electrical Activity of Human Muscle, 15 Ergonomics, 417, (1972).

Whitley et al., Influence of Three Different Training Programs on Strength and Speed of Limb Movement, 37 Research Quarterly, 132, (1966).

Kennedy, Substitution of the Tensiometer for the Dynanometer in Back and Leg Lift Testing, 30 Research Quarterly, 179, (1959).

Beasley, Instrumentation and Equipment for Quantitative Clinical Muscle Testing, 36 Archives of Physical Medicine and Rehabilitation, 604, (1956).

Literature of J. A. Preston Corp., undated, believed to be prior art.

Literature of Mycron Medical, Inc., re Myo-Metric II force sensor, undated.

Literature of Ametak for "Accuforce" digital force gauge, undated.

Literature of Abbey Medical for "Duratech Force Monitor", undated.

MANUAL MUSCLE TESTER

BACKGROUND OF THE INVENTION

This invention relates to the manual assessment of muscle strength. More particularly, the invention relates to a portable, manual muscle tester and to the method of using same.

Manual muscle testing is the most widely used method of physical examination for clinical evaluation of muscle strength. Manual tests are commonly used to monitor a patient's progress during an extended period of rehabilitation or recovery. These tests are also used to determine differences in strength between individuals and to determine strength deficits in a given individual. In the latter case, deficits are detected by the comparison of contralateral limb segments or muscle groups. Manual muscle tests are employed, as well, to locate weakness in areas not previously suspected by the patient. The area of weakness is often far removed from the site of pathology, and such weaknesses are related to the musclo-skeletal linkage systems of the body. Manual testing is also used in the design of rehabilitation or strengthening programs for individuals who have been injured or wish to undertake an activity for which they are not properly conditioned.

Typically an examiner (and by this is meant a physician, therapist, athletic trainer, or coach, for example) asks a patient to maintain a specific posture with the limb being tested. The examiner applies pressure downward with one or two hands and judges subjectively the patient's resistance. For example, the examiner may judge the force he must apply to a limb in order to lower it from a raised position. The resistance is quantified subjectively with a grade from 5 (maximal) to 0 (no contraction). For purposes of comparison, a patient's unaffected limb is similarly tested. From day to day or week to week, the examiner relies on a subjective determination to measure the patient's progress.

Manual muscle testing is essentially a subjective evaluation and is unreliable when performed by different individuals who may use different techniques. Several attempts to standardize manual testing procedures have been made and many devices to measure strength have been proposed. One of the earliest, which dates back to 1912, is a spring scale device. Lengthy reviews are now available on various devices and their use. Despite the obvious disadvantages of a subjective test of a muscle strength, manual muscle testing, without instrumentation, continues to be the predominant method used in the clinical setting. Until recently, few, if any, dynamometers (strength measuring devices) offered objective, accurate evaluation of dynamic muscle strength.

The patent literature proposes devices for measuring strength. For the most part, these are large, cumbersome, immobile, and specially adapted to test particular muscles, those of the legs, for example, or those of the arms. In one case, portability of a test device is recognized and a fluid filled cylinder and pressure gage arrangement is suggested. No provision is made for this device to retain the maximum pressure gage reading. A dial gage indicates force applied to the fluid cylinder plunger and typically these are much harder to read than a clear digital, numeric force indication, particularly when the indication quickly varies, as in all muscle testing procedures.

The physician, physical therapist, athletic trainer who tests a subject's strength is aware of what muscles contribute what forces and in what directions. A simple example clarifies the importance of selective measurement. A subject's leg is commonly tested by having the subject sit and raise his foot off the floor. The examiner applies pressure downward at the knee gradually until he overcomes the subject's resistance and the leg moves downward. The examiner is interested in those muscles resisting downward force. In this test, the examiner is not concerned, for example, with the forces resisting rotational movement from the hip to the knee, or those forces resisting movement of the leg from side to side. Likewise, the examiner does not want his measurement to include force components directed longitudinally along the upper leg to the hip. A manual muscle tester should permit the examiner to distinguish between the forces that are of interest, and those that are not.

For ease of operation, a portable manual muscle tester should be simply used, preferably in a manner closely akin to the testing that the examiner currently uses. The unit should be easy to operate without elaborate attachment to the patient or subject, should be easy to read, afford repeatability in its strength indications from one test to the next, should require no elaborate or time consuming setup procedure, and should be of a size, shape, and weight such that the examiner will readily keep it with him throughout the day.

BRIEF SUMMARY OF THE INVENTION

In accordance with this invention, an improved, manual muscle tester is provided. The unit is light weight, small enough to be held in one hand, accurate, and easily read. This instrument responds only to forces applied along an axis perpendicular to its face, it is battery operated, and its digital output freezes at the maximum measured force.

Under the direction of Dr. James A. Nicholas, a device for objectively quantifying muscle strength has been a longstanding goal of The Institute of Sports Medicine and Athletic Trauma (ISMAT). Dr. Nicholas began actively researching this problem when he realized the importance of measuring hip flexor strength in patients with osteoporosis. In this work, the following characteristics have been concluded to be important:

1. readily quantified muscle force outputs indicative of strength;
2. palm-sized, compact, and portable;
3. wireless;
4. not susceptible to eccentric loading.

The present invention meets the above objectives. It has a digital display that freezes at the peak force, and optionally an output analog signal as well. It is small and light. The unit is self contained, being battery operated and requiring no wires to a source or to auxiliary equipment. A uniquely constructed flexure to which the input force is applied and small integrated circuits contribute to the instrument's compactness. The flexure and a strain gage bridge circuit eliminate forces other than those applied in the chosen direction.

The size and weight of the instrument of this invention permit the examiner to use the same procedures with which he is familiar. In fact, since the examiner exerts force in much the same way as before, to test the patient's resistance, he or she need not entirely discard the subjective evaluations that may result from years of experience. In the test described above, for example, the examiner will still be aware of the force resisting downward movement of the leg when the force is applied through the instrument to the raised knee.

Because the subject unit is wireless as well as compact, it invites the examiner to carry it, to use it regularly, and to become accustomed to relying on the more objective indication of the patient's strength.

The input beam or "flexure" and the bridge circuit discard forces applied to the tester other than in a direction parallel the axis of movement of an actuator that the patient engages. The flexure is a cantilever beam connected to the manual actuator. The beam has four strain gages arranged thereon to form a bridge circuit. An output signal from the bridge circuit is proportional to force applied in the direction of actuator movement perpendicular to the beam. Forces other than the perpendicular forces are cancelled. The cantilever beam is constructed to prevent stresses being reflected back to the strain gages from the location where the beam is connected to its support. At its supported end, remote from the actuator, the beam is T-shaped. The arms of the T turn downward. At their down turned ends, the arms of the T-shaped beam adjoin a support block which supports the beam. The block is centrally recessed to allow the stem of the T-shaped beam to flex along its length from the actuator to its top where it joins the arms. By removing the support locations from the path of strain communicated along the stem from the actuator to the gages, this shape prevents reflected stress or stress introduced by the attachment of the beam and support block from contributing to the measurements made by the strain gages. The beam shape, moreover, contributes to the unit's compactness.

The output display of this manual muscle tester is located on the opposite side of its case from the actuator. This digital force indication faces away from the subject and towards the examiner for easy reading. Because, with each test, the digital force indication freezes at its maximum, the examiner can concentrate on properly testing his subject, rather than having to concentrate on reading the force indication during the test. In addition to the digital peak force indication, a force versus time analog signal is made available at an output jack and is suitable for recording or display.

Distinctly beneficial features reside in the circuitry that translates the force applied to the actuator into the digital display that the examiner reads. The digital meter circuit is ratiometric. It employs the same input or reference voltage as the strain gage bridge. Because the voltage being measured is derived from the same input voltage as the reference voltage applied to the meter, reference voltage changes do not contribute error, the ratio measured remains the same.

A calibration check is provided by switching a fixed resistance into parallel with one of the resistances of the bridge to provide an imbalance. If the electronics and batteries are in acceptable condition, a particular digital output will be displayed when the bridge is thus unbalanced.

The bridge output is supplied to an instrumentation amplifier. Its output supplies an operational amplifier of the peak freeze circuit. Special attention is given to preventing rapid discharge of a peak freeze capacitor storing the voltage from which the output display is derived. A second high input impedance operational amplifier connected in the feedback loop of the first operational amplifier helps maintain the charge on the peak freeze capacitor and compensates for the diode characteristics by including them in the feedback path of the amplifiers.

Depressing the reset switch has a two-fold purpose. It provides a discharge path for the peak freeze capacitor and it also connects the output of the peak freeze circuit to yet another amplifier which is wired as an integrator for automatically zeroing the electronics when there is zero force on the balance. The output of the integrator introduces a voltage to the reference input of the instrumentation amplifier with such a polarity that its output is driven to zero. During a test, the integrator maintains the proper no-load voltage to the instrumentation amplifier.

The above and further advantages of the invention will be better understood from the following detailed description of a preferred embodiment taken in consideration with the several figures of the attached drawings.

DESCRIPTION OF PREFERRED EMBODIMENT

Figure 1:
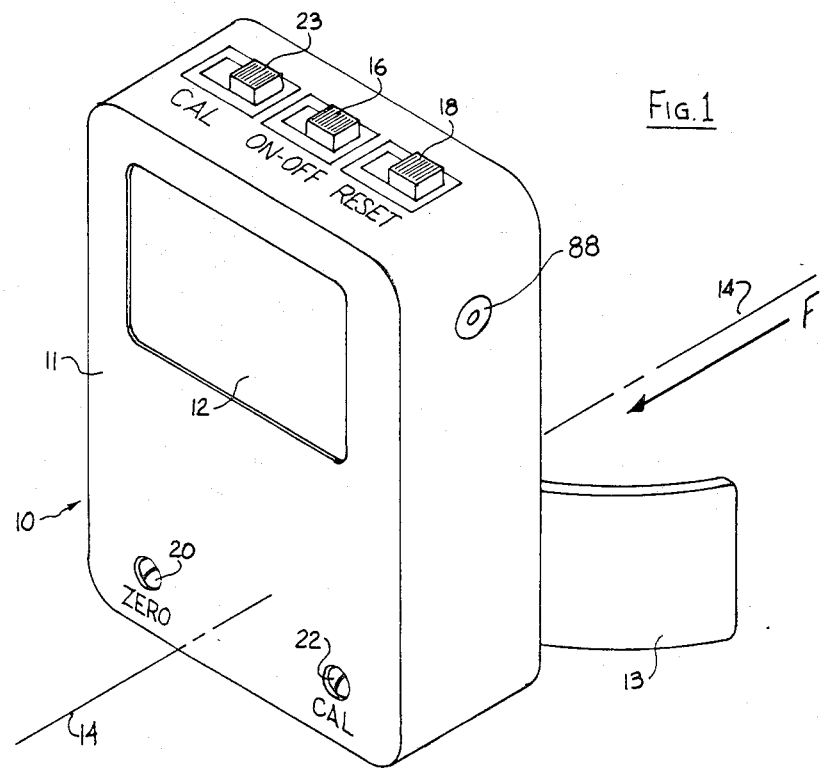
FIG. 1 is a perspective view of a manual muscle tester in accordance with the invention.
Figure 2:
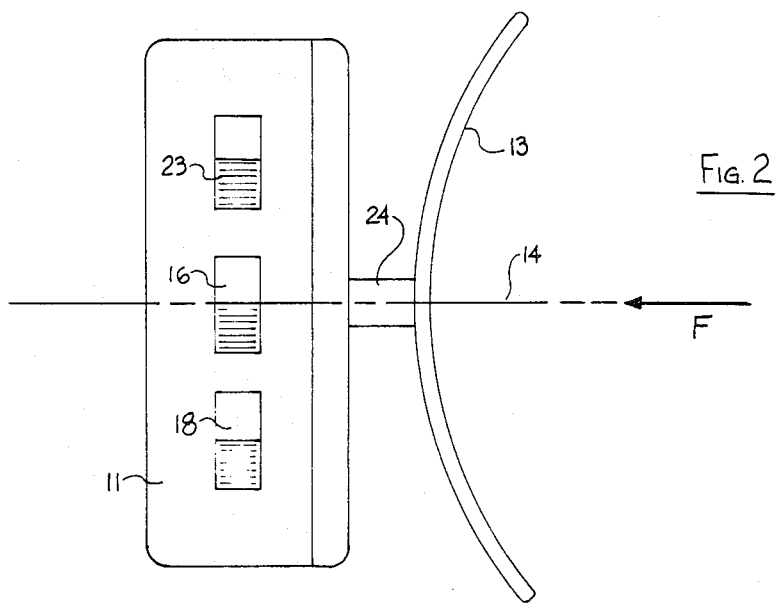
FIG. 2 is a top view of the instrument of FIG. 1.

In FIG. 1 a manual muscle tester 10 according to this invention includes a case 11 with a digital display 12 representing a force F applied to an actuator 13 parallel to the axis of movement 14 of the actuator. On the case of the instrument 10 can be seen, in FIG. 1, a switch 16. This is the unit's on-off switch. A switch 18 labeled "Reset" sets the meter back to zero as described more fully below. An adjusting screw 20 labeled "Zero" sets the display 12 at zero when no force is applied, and an adjustment screw 22 labeled "Cal" operates in cooperation with a switch 23 labeled "Cal" to calibrate the meter whose display is shown at 12.

Figure 3:
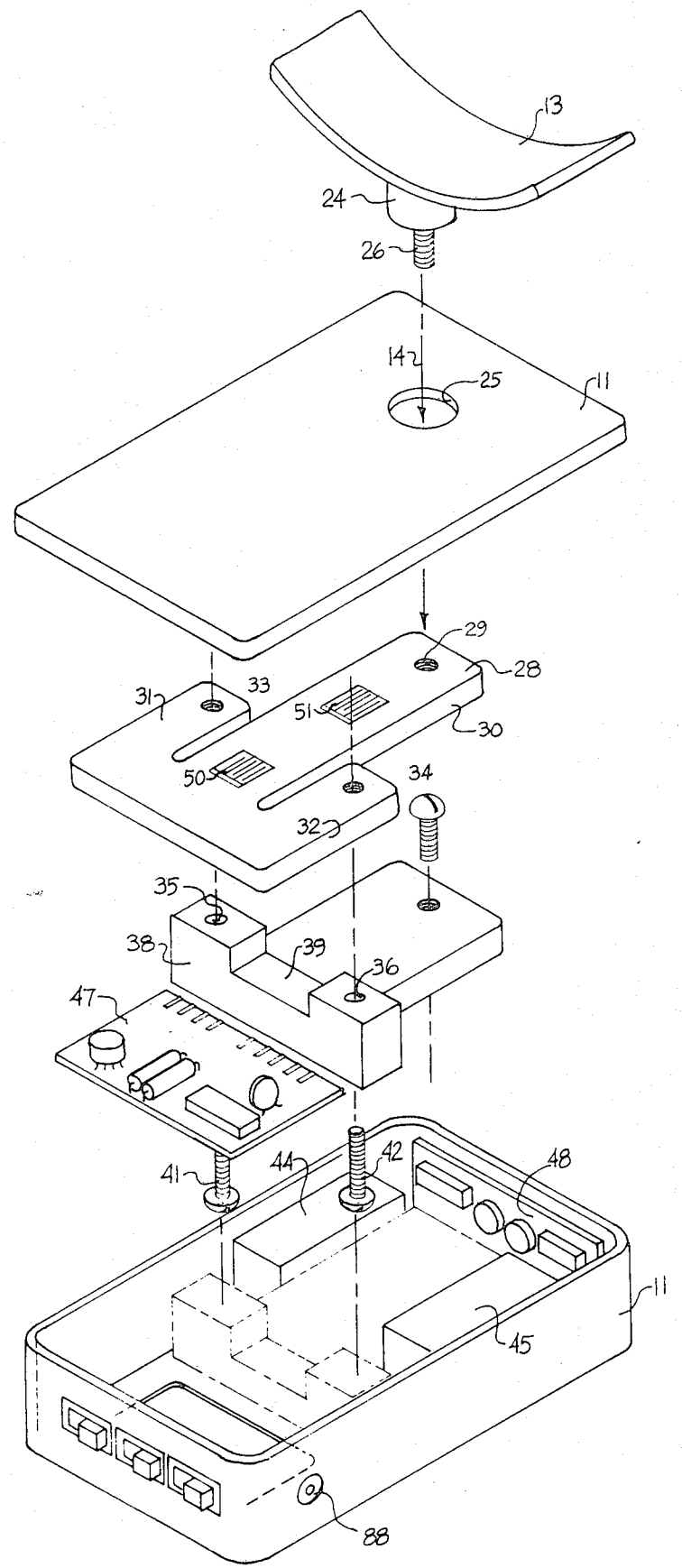
FIG. 3 is an exploded perspective view showing the shape of the flexure and the relationships of the parts of the instrument.

The actuator 13 has a stem 24 (FIG. 3) extending into an opening 25 in the case 11. The stem terminates in a threaded end 26 of reduced diameter as shown in FIG. 3. In this figure, one sees a cantilever beam or flexure 28 bored and tapped at 29 to receive the threaded end 26 of the actuator stem. The cantilever beam 28 has a T shape with down-turned arms 31 and 32. These have tapped and threaded openings 33 and 34 aligning with openings 35 and 36 in a mounting block 38. A pair of bolts 41 and 42 extend upward through the openings 35 and 36 and thread into the openings 33 and 34 to secure the down-turned arms of the T-shaped beam to the block 38, thus supporting the block in cantilever fashion. A recess 39 in the block 38 aligns with the longer central stem 30 of the T-shaped cantilever beam 28 and permits the beam's central stem 30 to flex downward between its arms 31 and 32 without interference by the mounting block.

In addition to the mechanical components of the instrument, in FIG. 3 one sees a pair of nine volt batteries 44 and 45 that power the unit. The printed circuit card 47 that is the digital volt meter whose display is shown at 12 in FIG. 1 appears in this Figure, and a printed circuit card 48 that cooperates with a strain gage bridge to translate input force to the analog signal read by the digital volt meter 47 appears, as well. In FIG. 3 two of the strain gages 50 and 51 that make up the bridge can be seen. Two further gages are similarly positioned on the under surface of central stem 30 of the beam 28.

Figure 4:
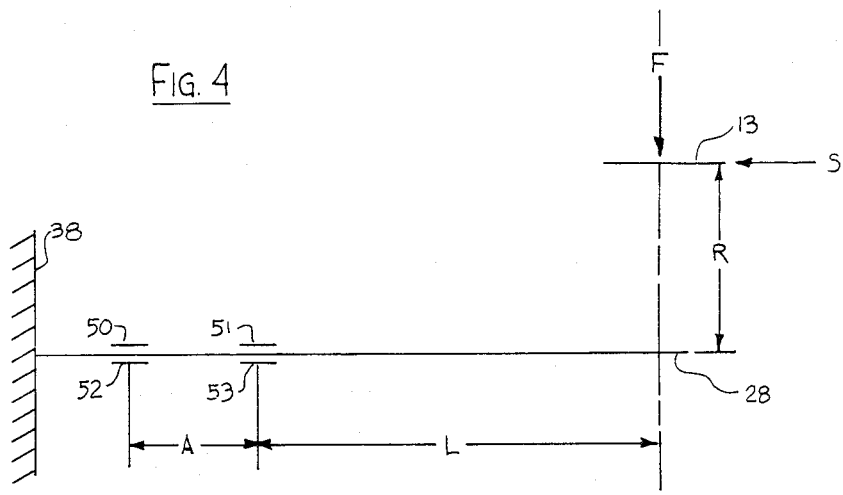
FIG. 4 is a diagrammatic illustration of the actuator, cantilever beam, and strain gage relationship.

The diagram of FIG. 4 illustrates the manner in which the beam 28, the actuator 13, and the strain gage bridge translate force parallel the axis 14 (or perpendicular to the face of the beam) into an electrical signal indicative of that force only. That parallel force is designated F in FIG. 4 and a force component perpendicular to the axis 14 is designated S. The two additional strain gages 52 and 53 are seen located spaced apart lengthwise on the stem 30 of the beam 28 directly below the gages 50 and 51. The four gages are connected together in a bridge circuit 55, illustrated in FIG. 6. A reference or input voltage is applied across the bridge from a junction 56 of the gages 51 and 50 to a junction 57 of the gages 52 and 53. A force indicative output signal V is taken from the remaining junctions 58 and 59.

The strain measurement $M_1$ in the beam 28 at the location of the gages 50 and 52 is:

$$M_1 = F(A+L) - SR,$$

where
F is the force normal to the beam (parallel the axis 14);
A is the distance between the two gage locations lengthwise of the beam;
L is the distance between the gages 51 and 53 and the stem 24;
S is the force parallel the beam (normal to the axis 14); and
R is the length of the stem.

The strain measurement $M_2$ at the gages 51 and 53 is:

$$M_2 = FL - SR.$$

As connected, the bridge subtracts the two measurements to arrive at $M_1 - M_2$. Substituting:

$$M_1 - M_2 = FA + FL - SR - FL + SR,$$

$$M_1 - M_2 = FA.$$

Therefore, the bridge output is directly proportional to F, the force normal to the beam.

Figure 5:
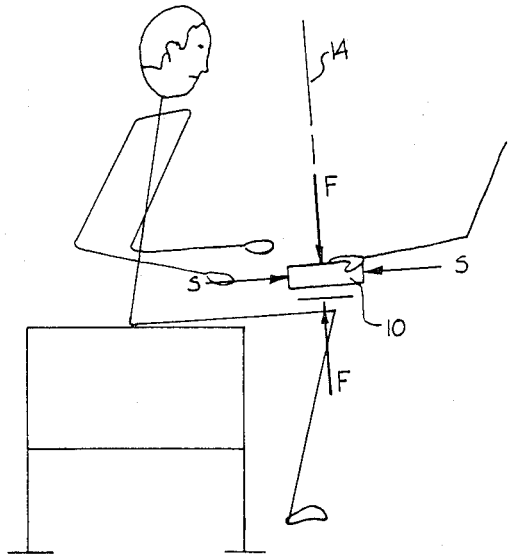
FIG. 5 is a diagrammatic and shows one manner of using the manual muscle tester.

In FIG. 5 a typical test procedure is shown. The patient or test subject sits, elevates his leg and resists the downward force F applied by the examiner. The peak force F which will appear and remain on the display of the meter of the unit 10 will be the force needed to overcome the patient's resistance and move the knee downward. The forces S transmitted substantially parallel the upper leg from knee to hip will not contribute to the force measured by the instrument. This force, communicated back along the femur to the hip, is only the resistance of the patient to movement backward on the table and is no part of the force F that the muscles exert in resistance to the examiner's downward force F.

Figure 6:
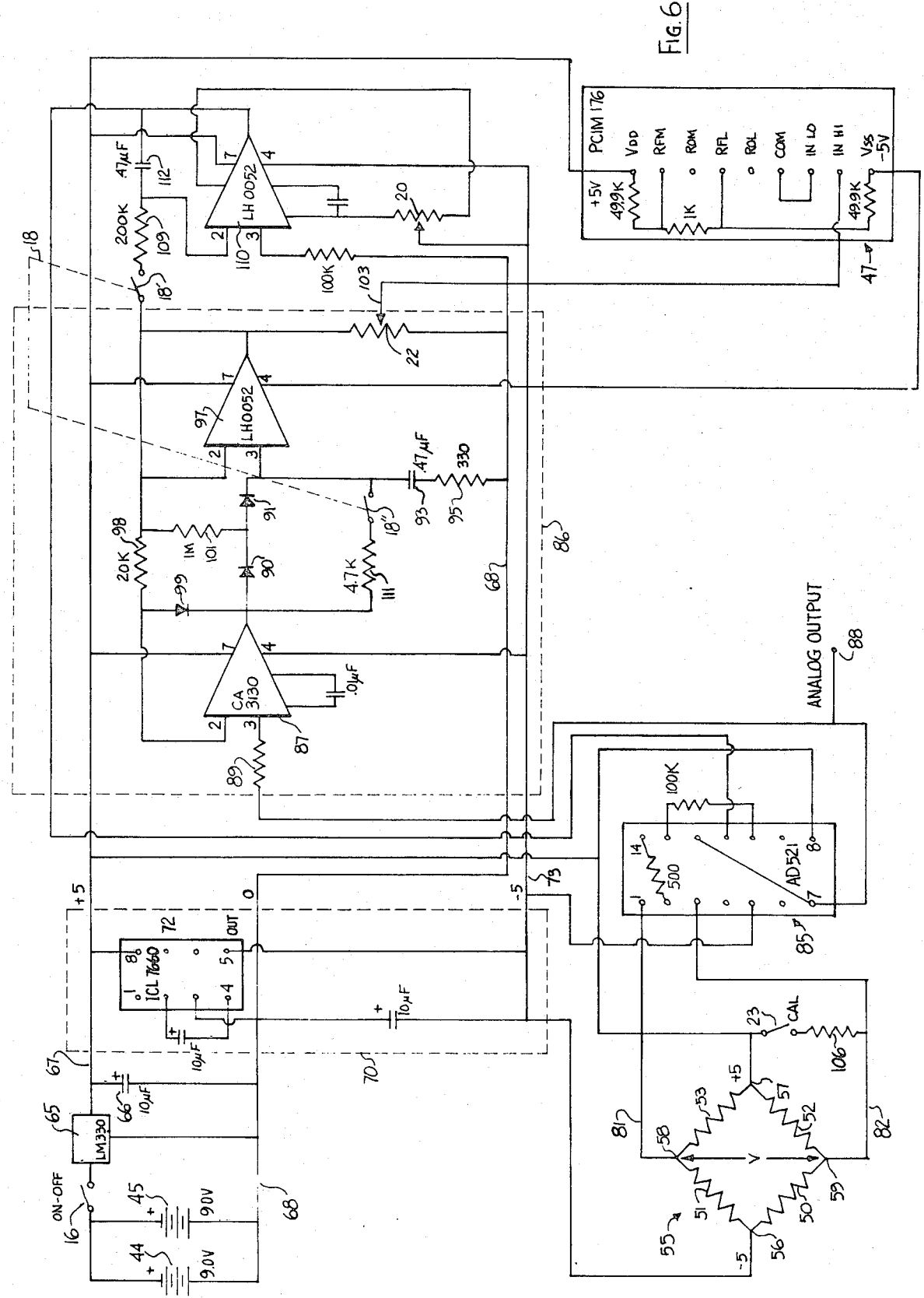
FIG. 6 is a schematic of the circuit that translates the input force to the digital display.
Figure 6:
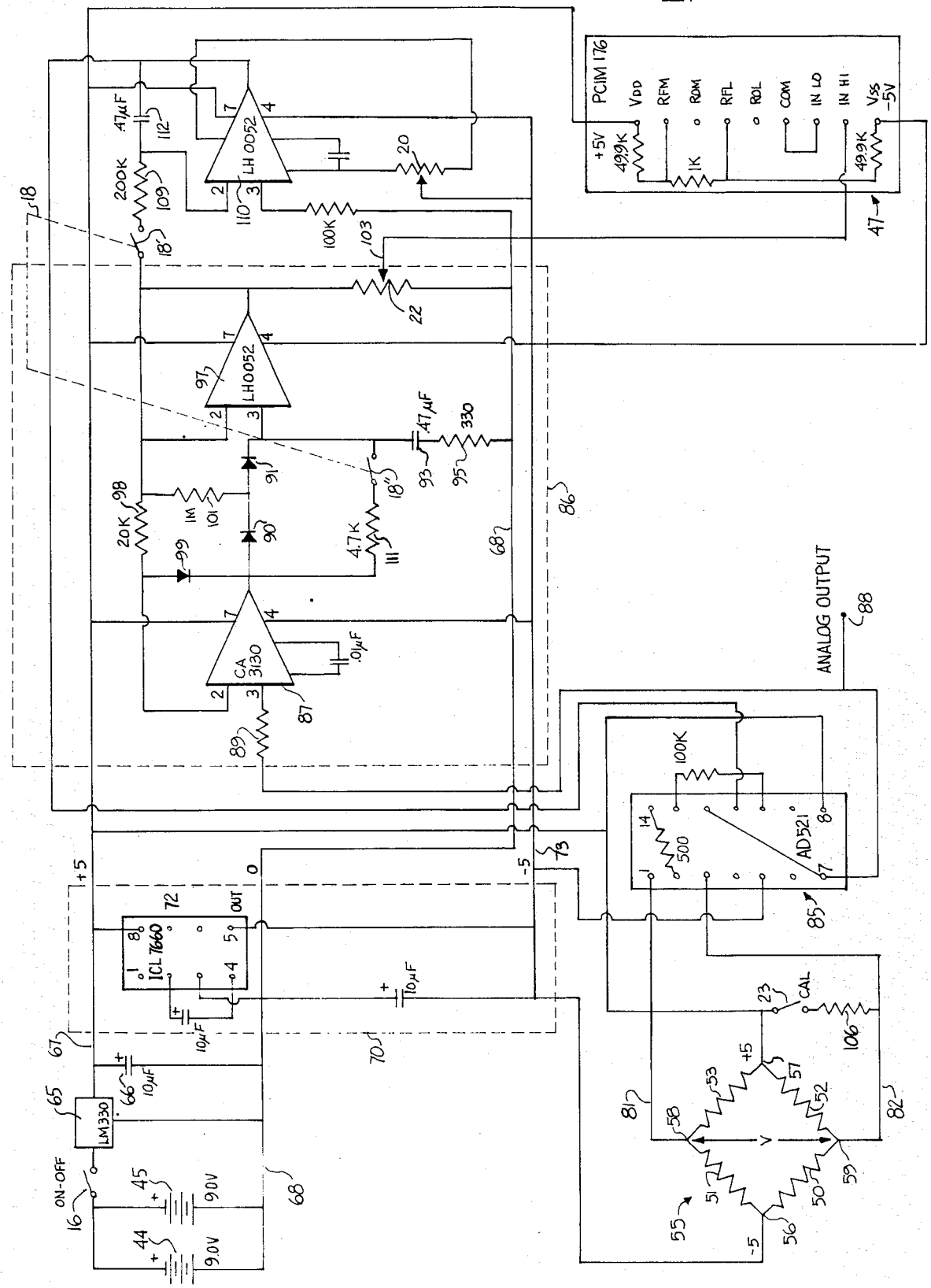

FIG. 6 illustrates the circuitry of the manual muscle tester. The two small nine volt batteries 44 and 45 supply the circuit through the on-off switch 16. A commercial voltage regulator 65 (National Semiconductor LM330, for example) provides a positive five volts across a capacitor 66 connected between a positive input or supply line 67 and a zero volt reference or supply line 68. A voltage convertor 70 serves as a power supply. Connected in its conventional manner between the lines 67 and 68 a commercially available integrated circuit 72 (such as the ICL 7660 of Intersil) provides a negative five volts to a line 73. The ten volts between line 73 and the line 67 are supplied as the input to the strain gauge bridge 55.

The bridge output, at junctions 58 and 59, is applied, via lines 81 and 82 to input terminals of an instrumentation amplifier 85 (e.g. Analog Devices AD521). The amplifier 85 is connected to provide a gain of 200. The output of the instrumentation amplifier is fed via resistance 89 to a "peak freeze" or peak detection circuit 86. This output is made available, for example, at a jack 88, as an analog output suitable for recording and/or display. The analog representation represents force throughout the time of the test procedure and does not freeze at peak force.

The peak detection circuit 86 includes a first operational amplifier 87 (such as RCA's CA 3130). The amplifier is connected to have a gain of one. A pair of diodes 90 and 91 connect the output of the operational amplifier 87 to a 0.47 µf peak freeze capacitor 93. The diodes prevent discharge of the peak reading or peak freeze capacitor. The peak freeze capacitor 93 and a 330 ohm resistor are connected in series between the zero volt reference line 68 and an input to a second operational amplifier 97 (e.g., National Semiconductor LH0052). This amplifier 97 is provided in the feedback loop of the first operational amplifier 87 along with a 20KΩ resistance 98. It is the output of this second operational amplifier 97 that, through the potentiometer 22, supplies the digital meter that indicates input force.

Inclusion of the second amplifier 97 protects the peak freeze capacitor 93 from bleed-off by virtue of its high input impedance. Use of the two diodes 90 and 91 allows a high resistance 101 to be connected between the feedback from the second operational amplifier to the junction of the two diodes. The resistance 101, one MΩ for example, keeps the anode side of the diode 91 at the same high voltage as the output of amplifier 97 after the output voltage from the amplifier 87 has dropped. This prevents drain-off of the peak freeze capacitor 93 by slight reverse current back through the diodes 90 and 91 when the input force to the manual muscle tester has been reduced and the output of the operational amplifier 87 drops.

Connection of the two diodes 90 and 91 along with the operational amplifier 97 in the feedback loop of the amplifier 87 also removes the "knee" or nonlinear portion of the characteristic curve of the diodes to produce a much more linear relation between the input to the peak freeze circuit and its output. By virtue of the apparent lack of feedback the gain of the peak freeze circuit, which can be viewed as a single amplifier, increases dramatically in the low voltage region, where the diode "knee" is evident, until the output is clamped at the input voltage. A diode 99 connected from the output of the operational amplifier 87 to the feedback path connection that amplifier's inverter terminal prevents the output of that amplifier from going negative during the zeroing and meter resetting described below.

The adjustable arm 103 of the potentiometer 22 provides the input to the digital meter 47. The meter is a digital volt meter (e.g., Printed Circuit International's PCIM 176) with reference connections connected between the line 67 at positive five volts and the line 73 at negative five volts. The potentiometer 22 calibrates the meter. The meter connection is ratiometric; the meter reference voltage is the same ten volts as the bridge input. The meter compares the peak freeze output of the amplifier 97 with the ten volts across the bridge. Changes in the input or reference voltage affect proportionally the force indicative voltage applied to the meter and do not affect the ratio that the meter reads. Thus, such changes do not result in error in the displayed value.

Calibration of the meter is checked by closing a calibration switch 23. The switch is in series with a calibration resistance 106 and connects the resistance 106 in parallel with one of the strain gage resistances of the bridge. This imparts a standard imbalance to the bridge. Each time the calibrate switch 23 is closed, then, the same digital reading should appear on the meter. If this does not occur, correction is made at the potentiometer 22.

To reset the instrument to zero, having tested a patient and noted the force indicated by the meter, a double pole single throw reset switch 18 is closed. One pair of contacts 18' connects the output of the amplifier 97 through a resistance 109 to an input of yet another operational amplifier 110 (again, LH0052, for example). This amplifier is connected as an integrator. Its storage capacitor 112 in its feedback path stores the voltage necessary to produce a zero meter reading when no force is applied to the actuator 13. A variable resistance 20 is shown connected to the amplifier 110 in the manner that is conventional for adjusting offset voltage. This variable resistance has been adjusted initially, in the absence of any input force, to bring the meter 47 to zero. The adjusted offset voltage, stored by the capacitor 112, is the slight voltage needed to compensate, for example, slight error voltages such as may appear from the bridge or as offset voltages of the instrumentation and further operational amplifiers.

When the contacts 18' close, the negative integral that is the output of the zeroing amplifier 110 is supplied to pin 11 of the instrumentation amplifier 85. Pin 11 has a gain of one relationship with the output pin 7. Hence, the negative integral is applied as an input to the first of the operational amplifiers, amplifier 87. This drives the output of that amplifier 87 to zero and discharges the peak freeze capacitor 93 through a resistance 111 and the remaining contacts 18" of the double pole single throw reset switch 18. The output of the amplifier 97 becomes zero and the digital meter registers zero.

Thus it will be seen that a compact, easy to read, and accurate manual muscle tester is provided. The forces applied other than along the instrument actuator's axis of movement are cancelled. The circuitry translating the input force to the digital output display enhances easy reading through its peak detection "peak freeze" operation. An analog voltage is also provided so that a complete time history of a test may be recorded, written on a strip chart recorder, or otherwise displayed. The circuit is especially adapted to be largely impervious to input or reference voltage variations through its ratiometric meter operation. The size, arrangement of the physical package, and the few adjustments necessary make the instrument easy to use by physicians, physical therapists, trainers, and coaches, unskilled in the operation of complex instruments. Its manner of use is very much like the subjective manual muscle tests already familiar to many.

Although a specific, preferred embodiment has been described in detail, modifications within the spirit and scope of this invention will be readily apparent. For example, the analog peak reading circuiting of the "peak freeze" provisions can be accomplished digitally by, for example, analog to digital convention of the bridge output, storage of the peak value in memory and display or stored peak in units of force. Accordingly, the foregoing description of the preferred embodiment is not to be construed as limiting the scope of this invention as defined in the appended claims.

We claim:

1. A small, portable, and self-contained manual muscle tester including:
   (a) a housing of a size sufficiently small to be held in one hand,
   (b) force responsive actuator means extending externally of the housing,
   (c) means connected with the actuator means and housed in the housing for electrically measuring forces applied to the actuator means, and
   (d) indicating means connected to the means for electrically measuring, and housed in the housing for displaying the force measured by the means for electrically measuring, the means for electrically measuring including means for excluding forces other than in a given direction of application to the actuator means and providing to the indicating means an input representative of force components having substantially only the given direction.

2. The manual muscle tester of claim 1 wherein the means for electrically measuring comprises a cantilever beam and circuit means responsive to flexure of the beam for developing a force indicative electrical signal.

3. The manual muscle tester according to claim 1 wherein the means for electrically measuring forces comprises a cantilever beam having deflection sensitive elements secured thereon in a bridge circuit, the beam and bridge circuit forming the means for excluding forces based on their direction.

4. The manual muscle tester according to claim 3 wherein the deflection sensitive elements are four strain gages arranged in longitudinally spaced pairs on upper and lower surfaces of the cantilever beam and connected to form said bridge circuit, the means for electrically measuring further includes means for applying a D.C. potential across the bridge to develop a force indicative output voltage from the bridge, and means for converting the force indicative output voltage to an output voltage applied to the indicating means, the indicating means including a voltage responsive display.

5. The manual muscle tester according to claim 1 wherein the means for electrically measuring forces comprises a cantilever beam, said actuator means contacting the beam for applying force thereto, means for developing an electrical signal indicative of the force component applied to the beam in said given direction by the actuator means, and the indicating means includes a meter display responsive to the electrical signal for indicating force applied to the beam.

6. The manual muscle tester according to claim 1 wherein the means for electrically measuring comprises a cantilever beam, said actuator means contacting the beam near one end thereof for applying force thereto, means located on the beam and responsive to the force applied thereto by the actuator means, means for supporting the beam at at least one location located out of stress transmitting alignment with the location of the means located on the beam responsive to force, whereby the means responsive to the force applied thereto by the actuator means is free of forces contributed from the location of the means for supporting the beam.

7. The manual muscle tester according to claim 6 wherein the beam is T-shaped, the actuator means contacts the beam on its central stem near one end thereof, the means located on the beam responsive to the force applied thereto is located intermediate the one end and the arms of the T, and the means for supporting supports the beam on the arms thereof.

8. The manual muscle tester according to claim 6 wherein the beam is T-shaped, the actuator means contacts the beam on its central stem near one end thereof, the means located on the beam responsive to the force applied thereto is located intermediate the one end and the arms of the T, and the means for supporting supports the beam on the arms thereof, the arms of the T-shaped beam turn down in the direction in which the stem of the T extends, the means for supporting supports the beam on mounts beneath the down turned arms, and the mounts have a space between them to allow flexing of the stem of the beam between the mounts.

9. A portable manual muscle tester including:
(a) a housing;
(b) force responsive actuator means extending externally of the housing;
(c) means responsive to forces applied to the actuator means for providing an electrical signal representative of the force magnitude;
(d) means for displaying an indication of the magnitude of the force applied to the actuator means; and
(e) circuit means interconnecting the means responsive to forces for providing an electrical signal and the means for displaying, the circuit means including means for retaining a force indicative signal at its peak value, and means for deriving from the peak value the force indication displayed by the means for displaying, the means for retaining a force indicative signal at its peak value comprises a peak freeze circuit including a first operational amplifier, a peak freeze capacitor connected to the output of the first operational amplifier, and a second operational amplifier connected in a feedback circuit of the first operational amplifier and connected at its input to the peak freeze capacitor, and further including a means connected between the output of the second operational amplifier and the means for displaying for applying at least a portion of the peak value to the means for displaying, said second operational amplifier having a high input impedance preventing rapid drain off of the peak freeze capacitor.

10. The manual muscle tester according to claim 9 further comprising means making available an analog output signal of the variation of force with time independently of the means for displaying and the peak freeze voltage on said capacitor.

11. The manual muscle tester according to claim 9 wherein the means for displaying is a digital voltmeter for indicating a digital peak force indication.

12. The manual muscle tester according to claim 9 wherein the circuit means includes zeroing means for returning the retained force indicative signal to a level representing zero force and for returning the displayed force to zero.

13. A portable manual muscle tester including:
(a) a housing;
(b) force responsive actuator means extending externally of the housing;
(c) means responsive to forces applied to the actuator means for providing an electrical signal representative of the force magnitude;
(d) means for displaying an indication of the magnitude of the force applied to the actuator means; and
(e) circuit means interconnecting the means responsive to forces for providing an electrical signal and the means for displaying, the circuit means including means for retaining a force indicative signal at its peak value, and means for deriving from the peak value the force indication displayed by the means for displaying, the circuit means including zeroing means for returning the retained force indicative signal to a level representing zero force and for returning the displayed force to zero, a force signal amplifier intermediate the means responsive to forces applied to the actuator means and the means for retaining a force indicative signal at its peak value, the zeroing means including means for applying a zeroing voltage to an input of the force signal amplifier to return the output thereof and the signal held by the means for retaining to respective levels representing zero force, and the means for applying a zeroing voltage including an integrating operational amplifier having an input selectively connectable to the output of the means for retaining a force indicative signal at its peak value and having its output connected to said input of the force signal amplifier.

14. The manual muscle tester according to claim 13 wherein the means for retaining includes a capacitor and the zeroing means includes switching means for applying the output of the integrating amplifier to the force signal amplifier and for closing a discharge path to the capacitor.

15. A portable manual muscle tester including:
(a) a housing;
(b) force responsive actuator means extending externally of the housing;
(c) means responsive to forces applied to the actuator means for providing an electrical signal representative of the force magnitude;
(d) means for displaying an indication of the magnitude of the force applied to the actuator means; and
(e) circuit means interconnecting the means responsive to forces for providing an electrical signal and the means for displaying, the circuit means including means for retaining a force indicative signal at its peak value, and means for deriving from the peak value the force indication displayed by the means for displaying, the means responsive to forces applied to the actuator means for providing an electrical signal including a strain gage bridge circuit, input voltage means including means for supplying an input to the bridge circuit, and means intermediate the bridge and the means for displaying for converting the bridge circuit output to a voltage measured and displayed by the display means, the means for displaying comprising a ratiometric meter circuit, and an input to the bridge circuit being connected to the meter circuit as a reference voltage to which the electrical signal representative of the force magnitude is compared, whereby excursions in the force representative signal applied to the meter circuit that are derived from excursions in the input to the bridge circuit are at least substantially diminished in the comparative value displayed.

16. A method of manual muscle testing including engaging a test subject with an actuator forming a part of a manual muscle test instrument, converting the force applied in a substantially only a given direction between the subject and the actuator to an electrical signal, digitally displaying the magnitude of the force in the given direction by measuring the electrical signal so generated and displaying a force indication based on the signal measurement, the step of converting the force to an electrical signal including generating a signal representative of force applied in the given direction while excluding representations of force in other than the given direction.

17. A manual muscle testing instrument having a case of size sufficiently small to be grasped in one hand by a test administrator, the case having first and second broad faces spaced apart and joined by narrower sides, a shaft extending through one of the faces of the case for the application of force thereto, by a test subject, a digital force read-out display means on the further broad face of the case and positioned to present the visible digital display thereof towards a test administrator located on the opposite side of the instrument from a subject applying force to the shaft, a beam within the case and in force transmitting relation with the shaft near one end of the beam, mounting supports in the case longitudinally spaced from the shaft, the beam comprising a T-shaped cantilever member, the ends of the arms of the T formed by the beam being secured to the mounting supports, means mounted on the beam for providing an electrical output representative of substantially only forces applied axially along the shaft to the beam, circuit means connected to the means mounted on the beam for providing an input to the digital force read-out display means in response to the electrical output from the means mounted on the beam.

18. The manual muscle testing instrument according to claim 17 wherein ends of the arms of the beam are turned down in the direction of a central stem forming the stem of the T, the mounting supports comprising projections affixed to the ends of the arms, the mounting supports being spaced apart and located one on each side of the stem intermediate the top and bottom of the T and in noninterfering relation to the stem.

19. The manual muscle testing instrument according claim 17 further comprising an enlarged yoke at least several times the width of the shaft and affixed to the shaft for engagement by a test subject, the means mounted on the beam for providing an electrical output representative of substantially only forces applied axially along the shaft to the beam comprising a force responsive bridge means for cancelling from its electrical output indications of force components applied to the beam parallel the stem of the T-shape of the beam from the yoke via the shaft.

20. A small, portable and self-contained manual muscle testing instrument including:

(a) a housing having first and second broad faces spaced apart by narrower wall portions, (b) force responsive actuator means communicating between the interior and the exterior of the housing and having means located on the same side of the housing as the first broad face for engagement by a test subject whose muscular strength is to be assessed, (c) the second broad face comprising a relatively flat area for engagement by at least one hand of a test administrator in force transmitting relation to the instrument in opposition to force applied to the actuator means by the test subject, (d) transducer means within the housing connected with the actuator means for producing an electrical signal representative of the force applied between the subject and the administrator, and (e) digital display means for representing said force, said relatively flat area for engagement by at least one hand of a test administrator and the force responsive actuator means being opposite one another whereby a test administrator can manually exert force on the instrument via the second broad face, in a direction perpendicular to that face and in opposition to the force exerted by the test subject consistent with known subjective muscle tests to produce on the digital display means an accurate representation of the force developed between the administrator and the subject.

21. A small, portable and self-contained manual muscle testing instrument including:

(a) a housing having first and second broad faces spaced apart by narrower wall portions, (b) force responsive actuator means communicating between the interior and the exterior of the housing and having means located on the same side of the housing as the first broad face for engagement by a test subject whose muscular strength is to be assessed, the actuator means including a shaft extending through the first broad face substantially perpendicular to the first and second faces, (c) the second broad face comprising a relatively flat area for engagement by at least one hand of a test administrator in force transmitting relation to the instrument in opposition to force applied to the actuator means by the teset subject, (d) transducer means within the housing connected with the actuator means for producing an electrical signal representative of the force applied between the subject and the administrator, the transducer means comprising means for excluding forces other than forces substantially parallel the shaft, and (e) digital display means for representing said force, whereby a test administrator can manually exert force on the instrument via the second broad face, in a direction perpendicular to that face and in opposition to the force exerted by the test subject to produce on the digital display means an accurate representation of the force developed between the administrator and the subject and whereby the force receiving surface of the second face permits the administrator to apply forces perpendicular thereto, and the perpendicularity of the shaft and the faces and the means for excluding forces provide a relatively accurate indication of forces developed between the subject and the administrator in a desired direction.

* * * * *